(12) United States Patent
Bedor

(10) Patent No.: US 8,403,970 B1
(45) Date of Patent: Mar. 26, 2013

(54) CERVICAL PLATE SYSTEM AND METHOD

(76) Inventor: Bernard M. Bedor, Ponte Vedra Beach, FL (US)

( * ) Notice: Subject to any disclaimer, the term of this patent is extended or adjusted under 35 U.S.C. 154(b) by 264 days.

(21) Appl. No.: 12/652,833

(22) Filed: Jan. 6, 2010

(51) Int. Cl.
*A61B 17/80* (2006.01)

(52) U.S. Cl. .................. 606/289; 606/280; 606/286

(58) Field of Classification Search .......... 606/280–299, 606/70, 71
See application file for complete search history.

(56) References Cited

U.S. PATENT DOCUMENTS

| | | | |
|---|---|---|---|
| 4,493,317 A | 1/1985 | Klaue | |
| 5,578,034 A | 11/1996 | Estes | |
| 5,741,258 A | 4/1998 | Klaue et al. | |
| 5,931,838 A | 8/1999 | Vito | |
| 6,224,602 B1 | 5/2001 | Hayes | |
| 6,454,771 B1 | 9/2002 | Michelson | |
| 6,503,250 B2 * | 1/2003 | Paul | 606/279 |
| 6,602,255 B1 | 8/2003 | Campbell et al. | |
| 6,602,256 B1 * | 8/2003 | Hayes | 606/296 |
| 6,652,525 B1 * | 11/2003 | Assaker et al. | 606/296 |
| 6,695,846 B2 | 2/2004 | Richelsoph et al. | |
| 7,115,130 B2 | 10/2006 | Michelson | |
| 7,306,605 B2 | 12/2007 | Ross | |
| 7,438,715 B2 | 10/2008 | Doubler et al. | |
| 7,452,370 B2 * | 11/2008 | Anderson | 606/296 |
| 7,468,069 B2 | 12/2008 | Baynham et al. | |
| 7,625,381 B2 | 12/2009 | Michelson | |
| 7,736,380 B2 | 6/2010 | Johnston et al. | |
| 7,963,982 B2 | 6/2011 | Kirschman | |
| 8,062,367 B2 | 11/2011 | Kirschman | |
| 2003/0187440 A1 | 10/2003 | Richelsoph et al. | |
| 2004/0097950 A1 * | 5/2004 | Foley et al. | 606/96 |
| 2004/0236335 A1 | 11/2004 | Michelson | |
| 2005/0234455 A1 * | 10/2005 | Binder et al. | 606/69 |
| 2006/0100626 A1 | 5/2006 | Rathbun et al. | |
| 2006/0122603 A1 | 6/2006 | Kolb | |
| 2006/0200146 A1 | 9/2006 | Doubler et al. | |
| 2007/0043369 A1 * | 2/2007 | Wallenstein et al. | 606/69 |
| 2007/0083203 A1 * | 4/2007 | Ribeiro | 606/69 |
| 2008/0287999 A1 | 11/2008 | Markworth | |
| 2009/0024170 A1 | 1/2009 | Kirschman | |
| 2009/0062863 A1 | 3/2009 | Peppers | |
| 2009/0182383 A1 | 7/2009 | Prybyla et al. | |
| 2009/0210010 A1 | 8/2009 | Strnad et al. | |
| 2009/0234393 A1 * | 9/2009 | Sournac et al. | 606/286 |
| 2010/0049256 A1 | 2/2010 | Jeon et al. | |
| 2011/0238123 A1 | 9/2011 | Kirschman | |
| 2012/0035657 A1 | 2/2012 | Kirschmaan | |

FOREIGN PATENT DOCUMENTS

WO 2008094572 A2 8/2008

* cited by examiner

*Primary Examiner* — Kevin T Truong
*Assistant Examiner* — Si M Lee
(74) *Attorney, Agent, or Firm* — Roetzel & Andress; Jason S. Miller

(57) ABSTRACT

A cervical plate system (1) and method for use in the fixation of a spine comprising a fixation plate (2) having a aperture (3) extending from a bone fixation plate (2) top surface (5) to a bottom surface (12), dimensioned for admitting a bone fixation element (4) shank (15) therethrough and smaller than a bone fixation element (4) head (16) for retaining the head (16) within the aperture (3); and a locking plate (11) positioned adjacent to a surface of the fixation plate (2) and dimensioned for slidable movement along a lateral axis (13) of the fixation plate surface, from a first position wherein the locking plate (11) disengages at least a portion of the bone fixation element (4) to a second position wherein the locking plate (11) engages at least a portion of the bone fixation element (4).

4 Claims, 5 Drawing Sheets

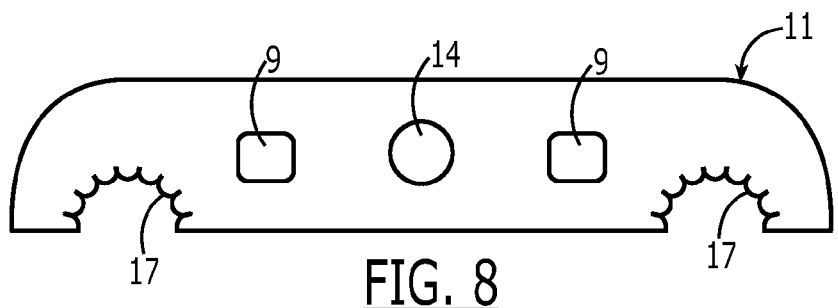
FIG. 8
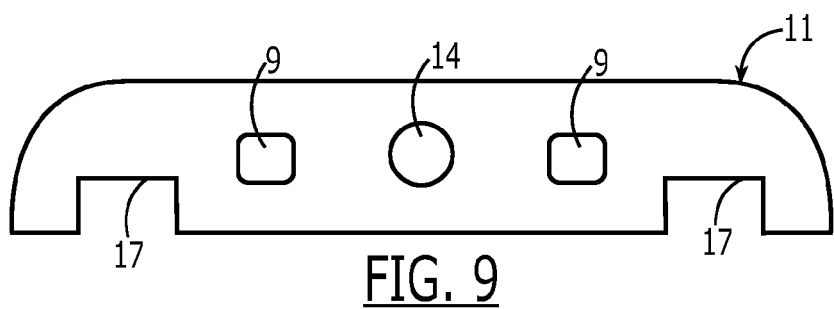
FIG. 9
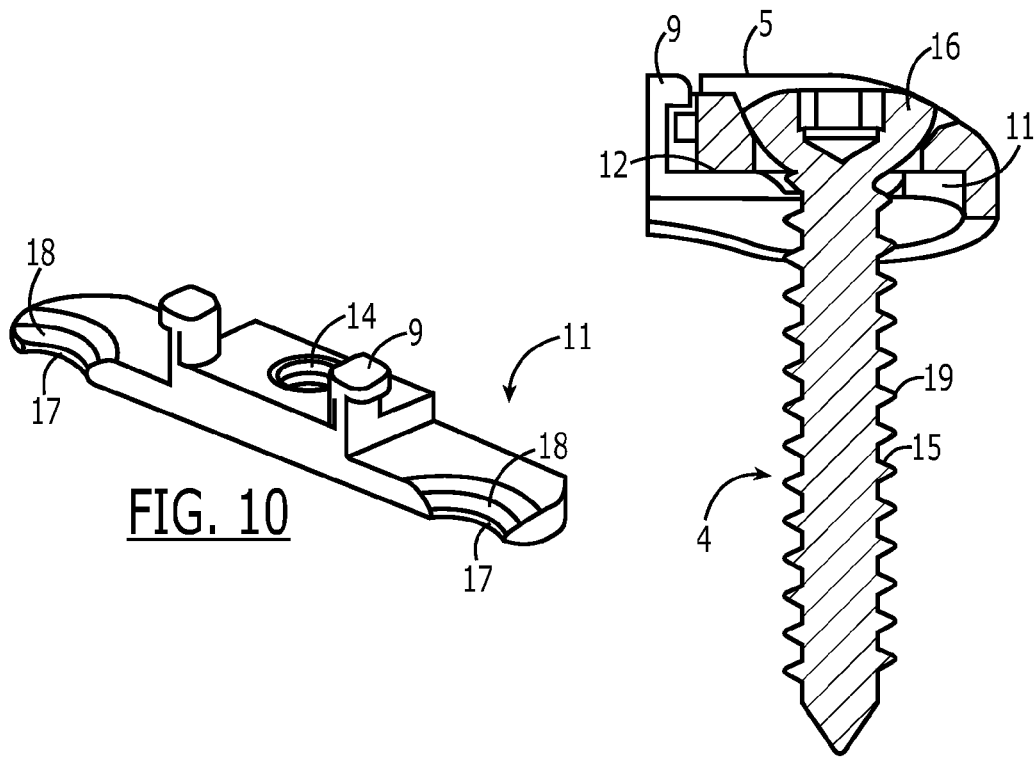
FIG. 10
FIG. 11

US 8,403,970 B1

CERVICAL PLATE SYSTEM AND METHOD

BACKGROUND OF THE INVENTION

1. Field of the Invention

The present invention relates to cervical plate systems and methods, more specifically, a cervical plate system that provides retention of a bone fixation element wherein vertical movement of the bone fixation element is significantly reduced.

2. Description of Related Art

Cervical spine surgery is a neurosurgical procedure for treating a wide variety of cervical spine disorders and deformities, including, but not limited to, cervical deformation, disc degeneration, arthritis, and congenital defects. In addition, cervical spine surgery is utilized to treat cervical fractures, injuries, or other traumas to the spine wherein the spine becomes displaced or otherwise altered from such fracture, injury, or trauma.

The procedure utilizes synthetic devices to anchor two or more vertebrae to one another in the spinal column. Such devices may include bone fixation elements, also referred to as bone screws, coupled to a fixation plate. The bone fixation elements are positioned within apertures located in the fixation plate are driven into the desired vertebrae. Such devices are typically temporary devices used to stabilize bone fragments or bones to one another until the fragments heal and/or the bones are fused to one another. As the ultimate goal of utilizing such synthetic devices is to limit movement of the cervical spine to promote healing, it is of great importance that fixation between the bone fixation element and fixation plate be secure.

Various structures for securing fixation plates to vertebrae are currently available wherein bone fixation elements are inserted through apertures located in the fixation plate and driven into the vertebrae. A problem associated with utilizing such bone fixation elements in cervical plate systems, however, is "backing out" wherein movement of the bone fixation element(s) occur. Such backing out may be in reference to movement of the bone fixation element in a vertical, horizontal, lateral, rotational, or any other direction of movement post-insertion of the bone fixation element into the bone.

To minimize such movement, various cervical plate systems include the use of locking plates wherein the locking plate is adjusted so as to cover the head of the bone fixation element once the bone fixation element has been inserted into the bone. In this manner, vertical movement of the bone fixation element is limited due to the head of the bone fixation element abutting the locking plate. Although use of a locking plate that covers the head of the bone fixation element prevents vertical backing out of the bone fixation element to a certain degree, vertical backing out is possible if there exists a distance between the top surface of the head of the bone fixation element and the bottom surface of the locking plate adjacent to the bone fixation element head. Moreover, locking plates that cover the head of the bone fixation element may not prevent or minimize backing out in other directions, such as horizontal, lateral, rotational, or other directional movement of the bone fixation element.

Thus, there exists a need for an improved cervical plate system that minimizes movement of a bone fixation element after its insertion into the bone.

SUMMARY OF THE INVENTION

The present invention is directed to a cervical plate system having a fixation plate having an aperture extending from a top surface of the fixation plate to a bottom surface of the fixation plate and dimensioned for admitting a shank of a bone fixation element therethrough and smaller than a head of the bone fixation element for retaining the head within the aperture, the shank extending downwardly from the bone fixation element; and a locking plate positioned adjacent to a surface of the fixation plate and dimensioned for slidable movement along a lateral axis of the fixation plate surface, from a first position wherein the locking plate disengages at least a portion of the bone fixation element to a second position wherein the locking plate engages at least a portion of the bone fixation element.

The present invention is also directed to a method for fixating a spine comprising positioning a fixation plate adjacent to a bone in a spine; inserting a bone fixation element into an aperture of the fixation plate such that a portion of the bone fixation element is located within the aperture and is adjacent to the bone; driving the bone fixation element into the bone such that at least a portion of a shank of the bone fixation element extends through the aperture and into the bone; sliding a locking plate in a lateral direction relative to the fixation plate from a first position wherein the locking plate disengages at least a portion of the bone fixation element to a second position wherein the locking plate engages at least a portion of the bone fixation element; inserting a securing element through a slot in the fixation plate and into the locking plate; and securing the securing element within the locking plate to secure the locking plate in the second position.

BRIEF DESCRIPTION OF THE DRAWINGS

FIG. 8 is a top view of a locking plate of the cervical plate system of the present invention;

FIG. 9 is a top view of a locking plate of the cervical plate system of the present invention;

FIG. 10 is a perspective view of a locking plate of the cervical plate system of the present invention; and FIG. 11 is a cross-sectional view of a cervical plate system of the present invention utilizing a locking plate as shown in FIG. 10.

DETAILED DESCRIPTION OF THE PREFERRED EMBODIMENTS

A description of the preferred embodiments of the present invention will now be presented.

Figure 1:
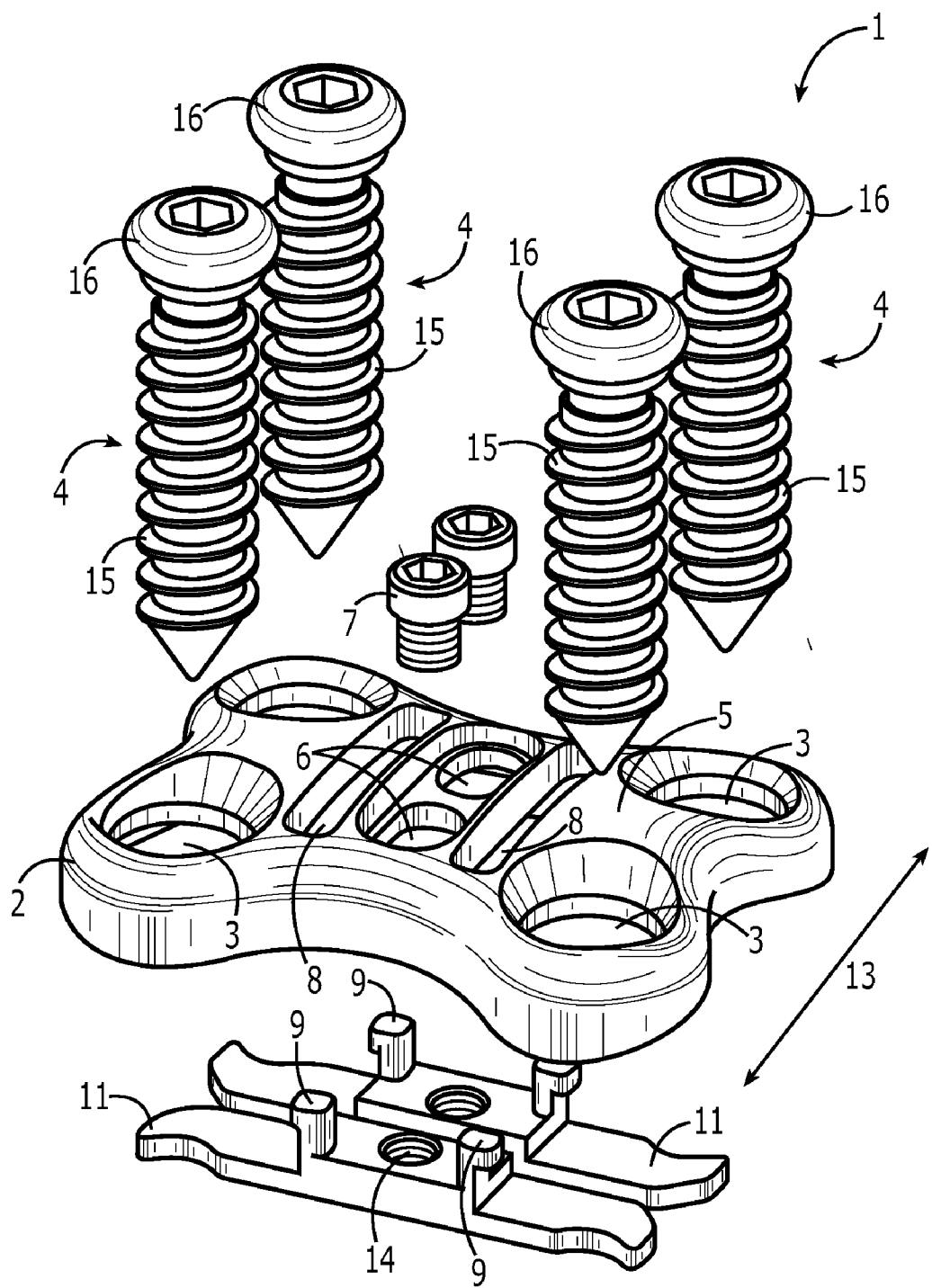
FIG. 1 is an isometric exploded view of a cervical plate system of the present invention.

With reference to FIG. 1, an isometric exploded view of a cervical plate system of the present invention is shown. The cervical plate system 1 includes a fixation plate 2 having at least one aperture 3 for insertion of at least one bone fixation element 4 therethrough. The fixation plate 2 has a top surface 5 and may include at least one securing means slot 6. The securing means slot 6 may be sized and shaped to permit a securing element 7, such as a screw or other type of fastening means, to be inserted therein to secure a locking plate in a certain position as described below. The bone fixation element 4 may be a bone screw, screw, or any other type of fastening means.

The fixation plate 2 may also include at least one extension slot 8. The extension slot 8 may be sized and shaped to permit a user to manipulate a locking plate between engaged and disengaged positions as described below.

The bone fixation elements 4 extend through the apertures 3 of the fixation plate 2. When located within the apertures 3, a head 16 of the bone fixation element 4 is located in line with or below the top surface 5 of the fixation plate 2 while a shank portion 15 of the bone fixation element 4 extends downwardly for ultimate insertion into a bone.

The cervical plate system 1 also includes at least one locking plate 11 that is slidingly adjustable along a lateral axis 13 of the fixation plate 2. When the locking plate 11 is in a disengaged position, a sufficient amount of the aperture 3 is unrestricted to permit at least a portion of the shank 15 of a bone fixation element 4 to extend therethrough. When the locking plate ills in an engaged position, the locking plate 11 engages at least a portion of the bone fixation element 4; that is, the locking plate 11 abuts at least a portion of the head 16 and/or shank 15 of the bone fixation element 4. When in an engaged position, a securing element 7 may be used to secure the locking plate 11 in such engaged position.

Figure 3:
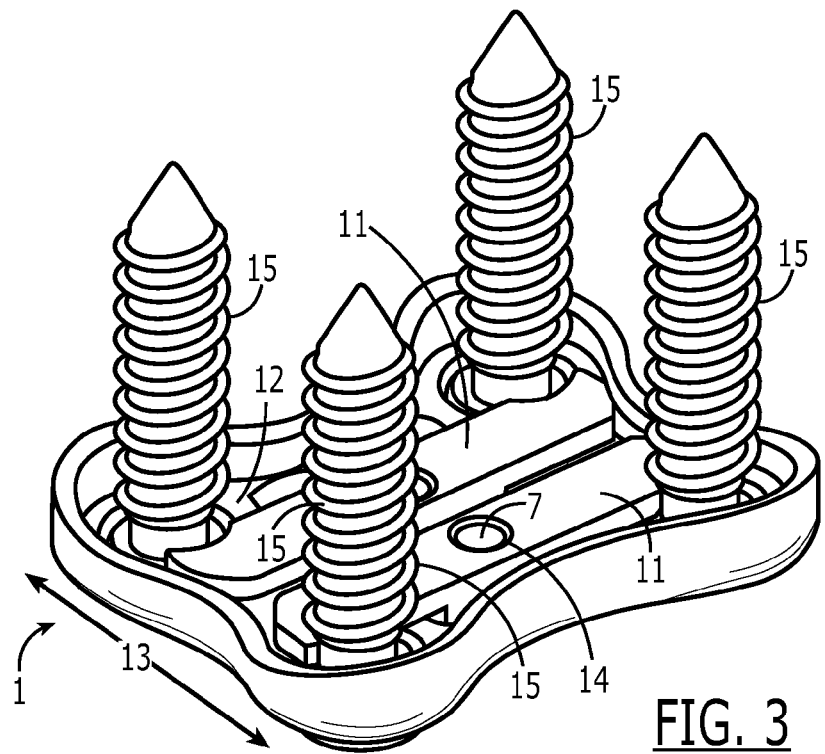
FIG. 3 is a perspective bottom view of the cervical plate system of the present invention.

The locking plate 11 may be located adjacent a bottom surface 12 (as illustrated in FIG. 3) of the fixation plate 2; however, the locking plate 11 may be located adjacent the top surface 5 of the fixation plate 2, or between the top surface 5 and the bottom surface 12. An aperture 14 may be located in the locking plate 11 to permit mating of the securing element 7 to the locking plate 11.

The locking plates 11 may also include at least one extension 9 sized and shaped for movement within the extension slot 8 in the fixation plate 2.

Figure 2:
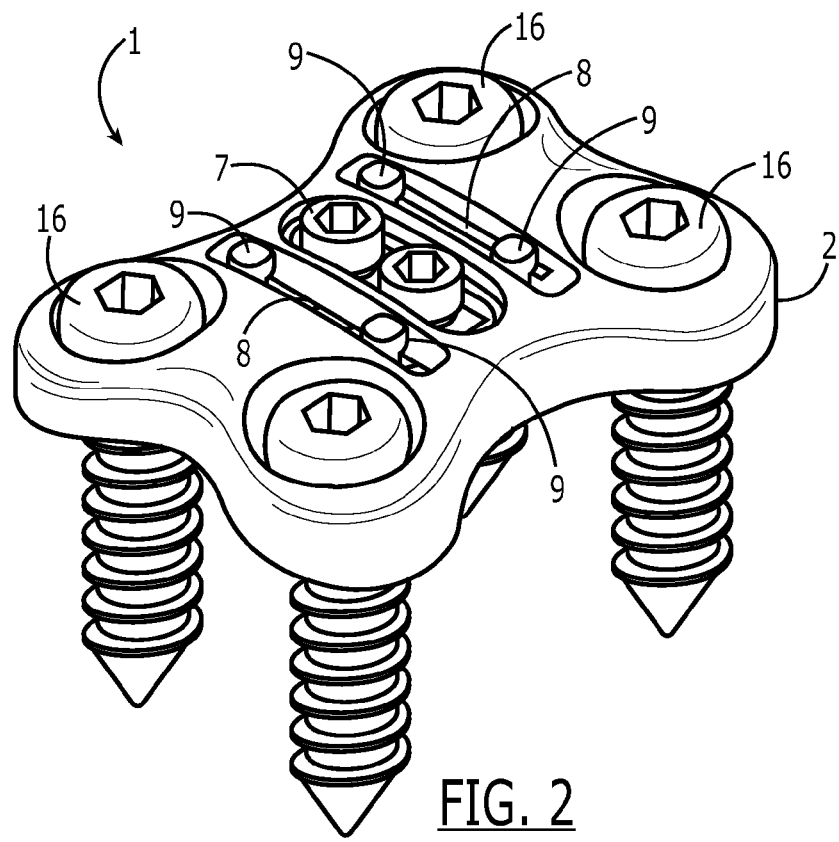
FIG. 2 is a perspective top view of the cervical plate system of the present invention.

In FIGS. 2 and 3 show perspective top and bottom views of the cervical plate system of the present invention, respectively. When assembled, the extensions 9 on the locking plates 11 are moveable within the extension slots 8 of the fixation plate 2. Additionally, once the locking plates 11 are positioned as desired, the securing elements 7 may be secured to the locking plates 11 so as to minimize movement of the locking plates 11.

Figure 4:
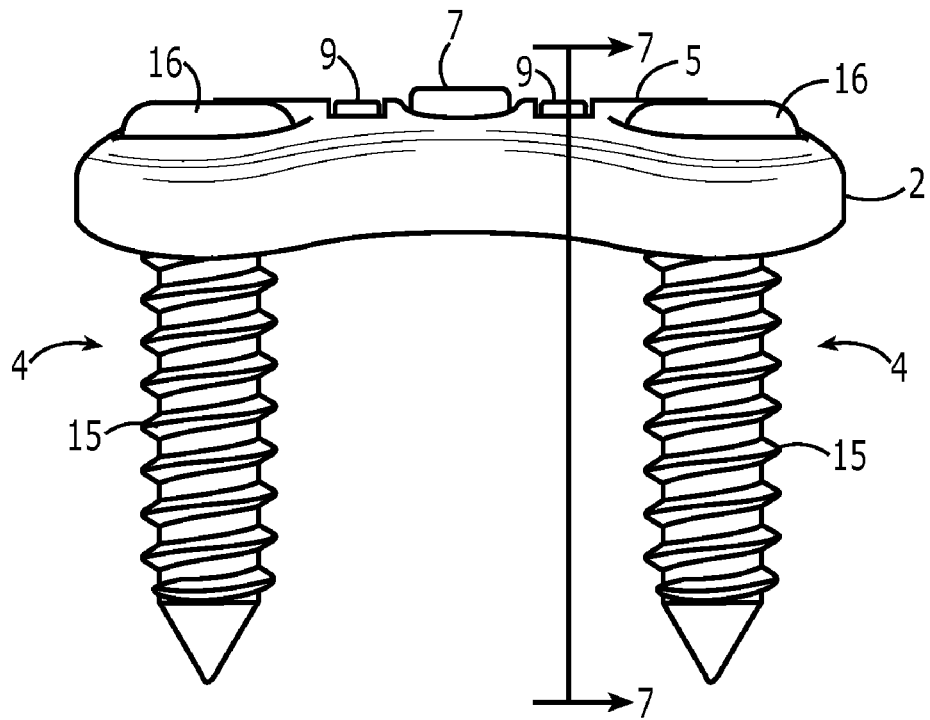
FIG. 4 is a frontal view of the embodiment of FIG. 2.

In FIG. 4, a frontal view of the embodiment of FIG. 2 is shown. The bone fixation elements 4 extend through the apertures 3 of the fixation plate 2. When located within the apertures 3, a head 16 of the bone fixation element 4 is located in line with or below the top surface 5 of the fixation plate 2 while a shank portion 15 of the bone fixation element 4 extends downwardly for ultimate insertion into a bone.

Figure 5:
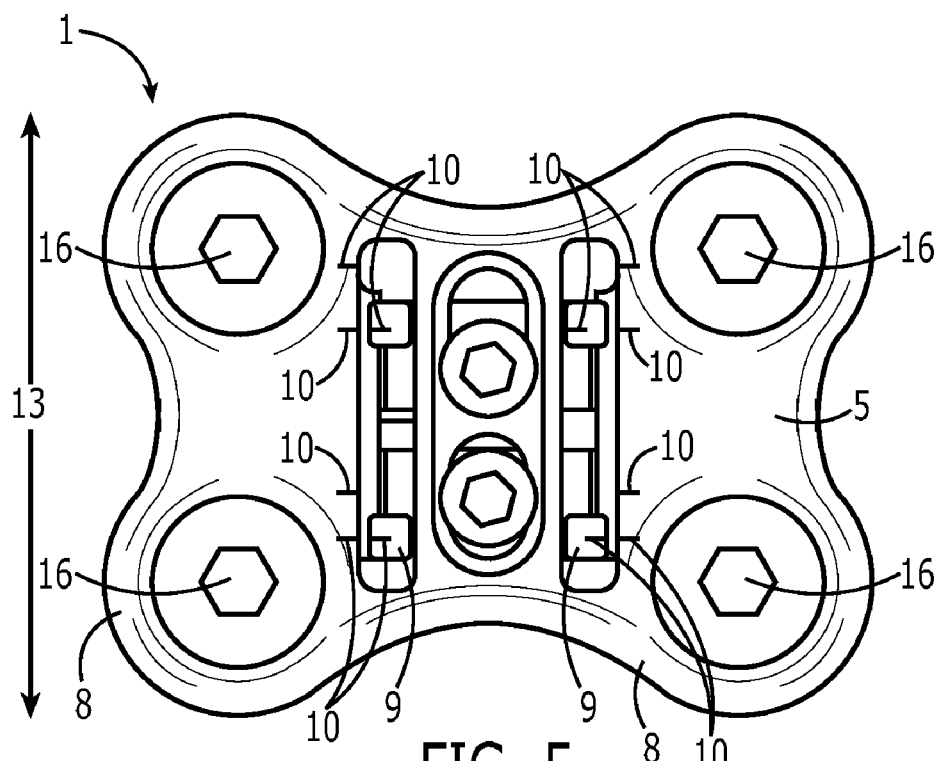
FIG. 5 is a top view of the cervical plate system of the present invention.

With reference to FIG. 5, a top view of a securing element the cervical plate system of the present invention is shown. At least one indicator 10 may be located on the fixation plate 2 and on the extension 9 to permit a user to easily determine whether a locking plate is in a first, disengaged position or in a second, engaged position. Specifically, the user aligns the indicator 10 located on the extension 9 to the desired indicator 10 located on the fixation plate 2. Other indicators 10 may be used on the fixation plate 2 and/or the extension 9 to indicate when the locking plate is in a first, disengaged position or a second, engaged position, including, but not limited to, symbols, words, notations, colors, numerals, and the like.

Figures 6, 7:
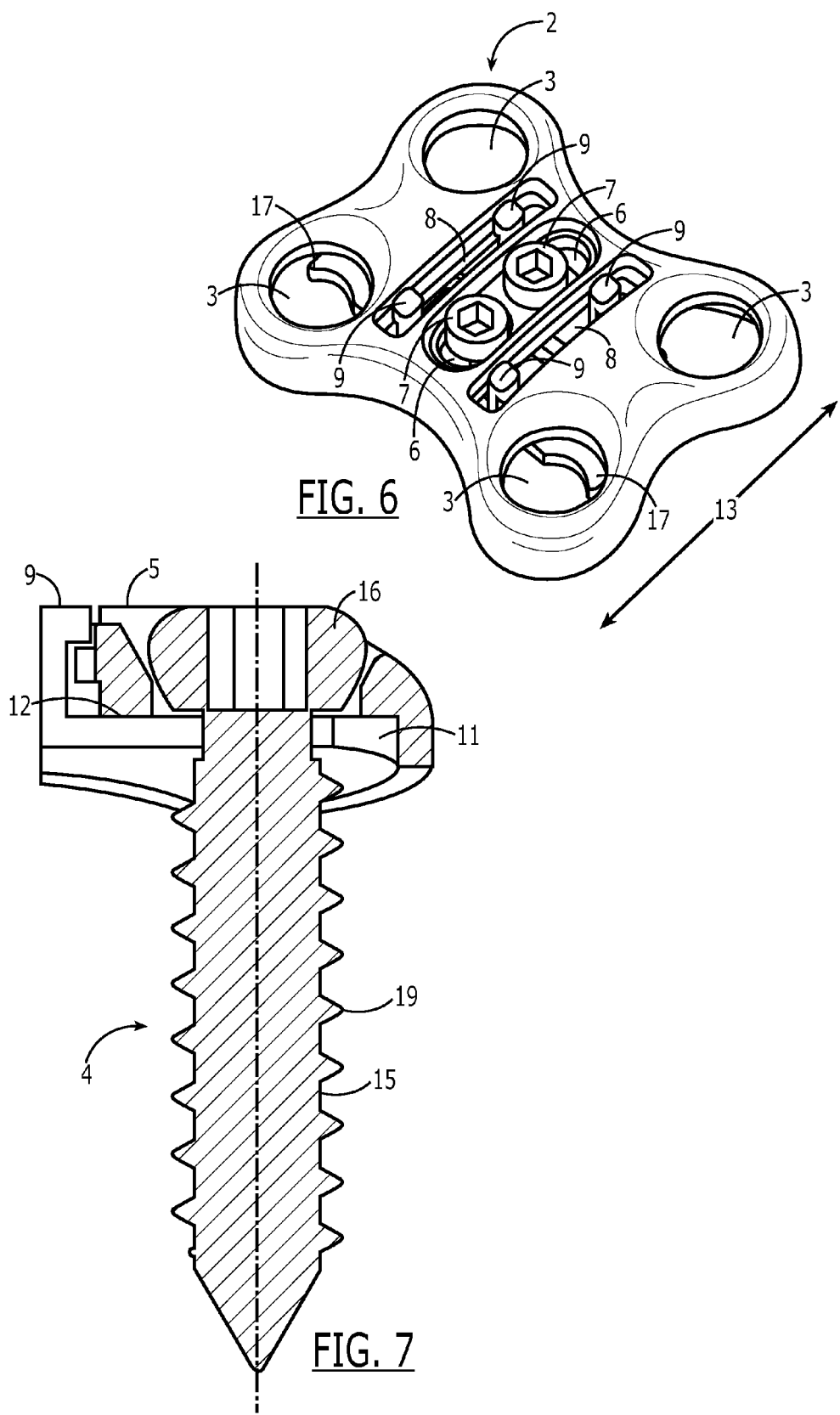
FIG. 6 is a top perspective view of the cervical plate system of the present invention without the bone fixation elements.
FIG. 7 is cross-sectional view along line 7-7 of the embodiment of FIG. 4.

With reference to FIG. 6, perspective top view of the cervical plate system of the present invention without the bone fixation element inserted therein is shown. As shown, the locking plate 11 includes semi-circular abutting edges 17 which abut at least a portion of the bone fixation element 4 when the locking plate 11 is in an engaged position.

Apertures 3 in the fixation plate 2 extend from the top surface 5 to the bottom surface 12 and are dimensioned for admitting at least portions of the shanks 15 therethrough and smaller than the heads 16 of the bone fixation elements 2 for retaining the heads 16 within the apertures 3.

The securing means slot 6 extends at least a portion along the lateral axis 13 and extends from the top surface 5 of the fixation plate 2 to the bottom surface 12 of the fixation plate 2. The securing element 7 extends through the securing means slot 6 for securing the locking plate 2 in an engaged position and is adapted for mating with the locking plate 11. For example, the securing element 7 may be secured to the locking plate 2 by mating the securing element 7 in an aperture 14 located in the locking plate 2. However, other securing means may be utilized.

The extension slot 8 extends at least a portion along the lateral axis 13 and extends from the top surface 5 of the fixation plate 2 to the bottom surface 12 of the fixation plate 2. The locking plate has a vertically extending extension 9 dimensioned for riding in the extension slot 8 to permit sliding of the locking plate 2 between an engaged and disengaged position.

When in an engaged position, the locking plates 11 engage at least a portion of the bone fixation element 2, such as the head 16 and/or the shank 15. Under some circumstances, the locking plate 11 may at least partially circumscribe the bone fixation element 4, specifically the head 16 and/or shank 15. Under other circumstances, the locking plate 11 may not partially circumscribe the bone fixation element 4, but rather merely abut at least a portion of the bone fixation element 4.

Next, FIG. 7 shows a cross-sectional view along lines 7-7 of the embodiment of FIG. 4. The cervical plate system 1 as shown features the locking plate 11 in an engaged position. The locking plate 11 is positioned adjacent to a surface of the fixation plate 2 and is dimensioned for slidable movement along the lateral axis 13 of the fixation plate 2. The locking plate 11 is slidingly secured to the bottom surface 12 of the fixation plate 2. When the locking plate 11 is in an engaged position, the locking plate 11 may exert a certain amount of force on the bone fixation element 4. Such force may be exerted on the head 6, the shank 15, and/or threads 19 of the bone fixation element 4.

FIGS. 8 and 9 show top views of locking plates of the cervical plate system of the present invention having abutting edges. The abutting edge 17 of the locking plate 11 may be semi-circular (as shown in FIGS. 1, 3 and 6), scalloped (as shown in FIG. 8) or semi-square/rectangular (as shown in FIG. 9). However, other shapes and designs are envisioned, including, but not limited to, those designs having teeth, grips, flanges, and other designs, and V-shapes, semi-hexigonal shapes, and other shapes. Having abutting edges 17 with certain designs or shapes may assist in retaining the bone fixation element 4 within the fixation plate 2; however, the invention does not require the abutting edges 17 to have particular designs or shapes.

FIG. 10 shows a perspective view of a locking plate of the cervical plate system of the present invention having beveled edges. The beveled edge 18 permits accommodation of the head 16 of the bone fixation element 4. Additionally, the beveled edge 18 permits a greater surface to surface contact between the bone fixation element 4, the locking plate 11, and the fixation plate 2, thereby reducing the amount of lateral, horizontal, and rotational movement of the bone fixation element 4.

Finally, FIG. 11 shows a cross-sectional view the cervical plate system of the present invention utilizing a locking plate as shown in FIG. 10. When utilizing a locking plate 11 having a beveled edge 18, the locking plate 11 may exert a certain amount of force on the bone fixation element 4. Such force may be exerted on the head 6, the shank 15, and/or threads 19 of the bone fixation element 4.

To use the cervical plate system 1 of the present invention to fixate a spine, a user first positions the fixation plate 2 adjacent to a bone in a spine. Then, the user inserts a bone fixation element 4 into an aperture 3 located in the fixation plate 2 such that a portion of the bone fixation element 4 is located within the aperture 3 and is adjacent to the bone. Next, the user drives the bone fixation element 4 into the bone such that at least a portion of the shank 15 extends through the aperture 3 and into the bone. The user then slides the locking plate 11 along the lateral axis 13 from the disengaged position to the engaged position wherein the locking plate 11 engages at least a portion of the bone fixation element 4. Next, the user inserts the securing element 7 through the securing means slot 6 and into the locking plate 11. Finally, the user secures the securing element 7 to the locking plate 11 to secure the locking plate 11 in the engaged position.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A cervical plate system comprising:
a fixation plate having an aperture extending from a top surface to a bottom bone contacting surface thereof and dimensioned for admitting at least a portion of a shank of a bone fixation element therethrough and smaller than a head of the bone fixation element for retaining the head within the aperture, the shank extending downwardly from the bone fixation element;
a locking plate positioned adjacent to the bottom bone contacting surface of the fixation plate and dimensioned for lateral slidable movement along a lateral axis of the fixation plate surface, from a first position wherein the locking plate disengages at least a portion of the bone fixation element to a second position wherein the locking plate engages at least a portion of the bone fixation element shank;
a securing means slot extending along at least a portion of the lateral axis, the securing means slot extending from the top surface to the bottom bone contacting surface; and
a securing element adapted for mating with the locking plate, the securing element extending through the securing means slot for securing the locking plate in the second position,
wherein the locking plate is slidingly secured to the bottom bone contacting surface of the fixation plate; and an extension slot extending along at least a portion of the lateral axis, the extension slot extending from the top surface to the bottom surface, wherein the locking plate has a vertically extending extension dimensioned for riding in the extension slot, for sliding the locking plate between the first and second position.

2. The cervical plate system of claim 1 wherein:
the locking plate at least partially circumscribes the bone fixation element shank when the locking plate is in the second position.

3. The cervical plate system of claim 1 wherein:
the locking plate at least partially circumscribes the bone fixation element shank when the locking plate is in the second position.

4. A cervical plate system comprising:
a fixation plate having:
a securing means slot extending at least a portion along a lateral axis, the securing means slot extending from a top end to a bottom end;
an extension slot extending along at least a portion of a lateral axis, the extension slot extending from the top end to the bottom end; and
the fixation plate having an aperture extending from a top surface to a bottom bone contacting surface of the fixation plate, and dimensioned for admitting a shank of a bone fixation element therethrough and smaller than a head of the bone fixation element for retaining the head within the aperture, the shank extending downwardly from the bone fixation element;
a locking plate positioned adjacent to the bottom bone contacting surface of the fixation plate and dimensioned for lateral slidable movement along a lateral axis of the fixation plate surface, from a first position wherein the locking plate disengages at least a portion of the bone fixation element to a second position wherein the locking plate at least partially circumscribes the bone fixation element shank when the locking plate is in the second position to engage at least a portion of the bone fixation element the locking plate; and
a securing element adapted for mating with the locking plate, the securing element extending through the securing means slot for securing the locking plate in the second position; and wherein the locking plate has a vertically extending extension dimensioned for riding in the extension slot, for sliding the locking plate between the first and second position.

* * * * *